US007195785B2

(12) United States Patent
Babish et al.

(10) Patent No.: US 7,195,785 B2
(45) Date of Patent: Mar. 27, 2007

(54) COMPLEX MIXTURES EXHIBITING SELECTIVE INHIBITION OF CYCLOOXYGENASE-2

(75) Inventors: John G. Babish, Brooktondale, NY (US); Terrence M. Howell, Lansing, NY (US)

(73) Assignee: Metaproteomics, LLC, San Clemente, CA (US)

( * ) Notice: Subject to any disclaimer, the term of this patent is extended or adjusted under 35 U.S.C. 154(b) by 13 days.

(21) Appl. No.: 10/480,145

(22) PCT Filed: Jun. 20, 2002

(86) PCT No.: PCT/US02/19617

§ 371 (c)(1),
(2), (4) Date: Oct. 13, 2004

(87) PCT Pub. No.: WO03/000185

PCT Pub. Date: Jan. 3, 2003

(65) Prior Publication Data

US 2005/0042317 A1 Feb. 24, 2005

(51) Int. Cl.
A01N 65/00 (2006.01)
(52) U.S. Cl. ..................................... 424/725
(58) Field of Classification Search ................. 424/725
See application file for complete search history.

(56) References Cited

U.S. PATENT DOCUMENTS

| | | | |
|---|---|---|---|
| 3,552,975 A | 1/1971 | Worden | |
| 3,720,517 A | 3/1973 | Bavisotto et al. | |
| 3,932,603 A | 1/1976 | Haas | |
| 3,933,919 A | 1/1976 | Wilkinson | |
| 3,965,188 A | 6/1976 | Westermann et al. | |
| 4,123,561 A | 10/1978 | Grant | |
| 4,133,903 A | 1/1979 | Thiele et al. | |
| 4,154,865 A | 5/1979 | Grant | |
| 4,401,684 A | 8/1983 | Versluys | |
| 4,554,170 A | 11/1985 | Panzer et al. | |
| 4,644,084 A | 2/1987 | Cowles et al. | |
| 4,692,280 A | 9/1987 | Spinelli | |
| 4,767,640 A | 8/1988 | Goldstein et al. | |
| 5,006,337 A | 4/1991 | Motitschke et al. | |
| 5,013,571 A | 5/1991 | Hay | |
| 5,073,396 A | 12/1991 | Todd, Jr. | |
| 5,082,975 A | 1/1992 | Todd, Jr. et al. | |
| 5,155,276 A | 10/1992 | Paul | |
| 5,166,449 A | 11/1992 | Todd, Jr. et al. | |
| 5,264,236 A | 11/1993 | Ogasahara et al. | |
| 5,286,506 A | 2/1994 | Millis et al. | |
| 5,296,637 A | 3/1994 | Stegink et al. | |
| 5,387,425 A | 2/1995 | Hsu et al. | |
| 5,604,263 A | 2/1997 | Tobe et al. | |
| 5,827,895 A | 10/1998 | Nutter et al. | |
| 6,020,019 A | 2/2000 | Ting et al. | |
| 6,129,907 A | 10/2000 | Sreenivasan et al. | |
| 6,383,527 B1 | 5/2002 | Artman et al. | |
| 6,391,346 B1 * | 5/2002 | Newmark et al. | .......... 424/756 |
| 6,583,322 B1 | 6/2003 | Shalai et al. | |
| 2002/0076452 A1 | 6/2002 | Babish et al. | |
| 2002/0077299 A1 | 6/2002 | Babish et al. | |
| 2002/0086062 A1 | 7/2002 | Kuhrts | |
| 2002/0086070 A1 | 7/2002 | Kuhrts | |
| 2003/0096027 A1 | 5/2003 | Babish et al. | |
| 2003/0113393 A1 | 6/2003 | Babish et al. | |
| 2003/0133958 A1 * | 7/2003 | Kuno et al. | ................. 424/401 |
| 2004/0137096 A1 | 7/2004 | Kuhrts | |
| 2004/0219240 A1 | 11/2004 | Babish et al. | |

FOREIGN PATENT DOCUMENTS

| | | | |
|---|---|---|---|
| DE | 19841615 | * | 3/2000 |
| JP | 04202138 | * | 7/1992 |
| JP | 406312924 | * | 11/1994 |
| JP | 07194351 | * | 9/2000 |
| RU | 2045955 | * | 10/1995 |

OTHER PUBLICATIONS

Chemistry and Analysis of Hop and Beer Bitter Acids, Elsevier, 1991, Eds., Verzele, M, and De Keukeleire, Chapters 5 and 6.*
Friedman, et al., J Cutan Med. Surg. 6(5):449-459 (2002).
Plewig, et al., J Invest. Dermatol. 65(6):532-536 (1975).
Jach, Przegl Dermatol. 65(4):379-382 (1978).
Bermejo, et al. Rev. Esp. Enferm. Dig. 95: 621-624 and 625-628 (2003).
Brown, et al. J Chem. Soc. 545 (1959).
Byrne, et al. J. Chem. Soc. (C):2810 (1971).
Carroccio, et al. Clin. Chem. 49:861-867 (2003).
Carson, J. Am. Chem. Soc. 73:1850-1851 (1951).
Charlier, et al. Eur. J. Med. Chem. 38:645-659 (2003).
Chou, et al. Adv Enzyme Regul 22:27-55 (1984).
Chou, et al. Eur. J. Biochem. 115:207-216 (1981).
Chou, et al. J. Biol. Chem. 252:6438-6442 (1977).
Chou, et al. J. Theor. Biol. 35:285-297 (1972).
Chou, J. Theor. Biol. 59:253-276 (1976).
Chou, et al. Trends Pharmacol. Sci. 4:450-454 (1983).
Costa, et al. Digest. Liver Dis. 35:642-647 (2003).
Goldstein, et al. Am. J. Gastroenterol. 96:1019-1027 (2001).
Halter, et al. Gut 49:443-453 (2001).
Hammberg, et al. J. Bio. Chem. 246:6713-6721 (1971).
Kanematsu, et al. J Bone Miner Res 12(11):1789-1796 (1997).

(Continued)

Primary Examiner—Michael Meller
(74) Attorney, Agent, or Firm—McDermott Will & Emer, LLP

(57) ABSTRACT

A novel formulation is provided that serves to specifically inhibit the COX-2 mediated inflammatory response in animals. The formulation comprises comprising an effective amount of component I selected from the group consisting of alpha acids and beta acids and an effective amount of at least one component II selected from the group consisting of alpha acids, beta acids, essential oils, fats and waxes, with the proviso that component I and II are not the same compound. The composition provides specific inhibition of cyclooxygenase-2 with little or no effect on cyclooxygenase-1.

11 Claims, No Drawings

OTHER PUBLICATIONS

Lopes, Curr. Med Res Opin. 8:145-149 (1982).
Meling, et al. Scand. J. Gastroenterol. 31:339-344 (1996).
Noreen, et al. J. Nat. Prod 61:2-7 (1998).
Thomas M. Newmark and Paul Schulick, Beyond Aspirin Nature's Answer to Arthritis, Cancer & Alzheimer's Disease, Hohm Press (2000).
Pairet, et al. Inflamm. Res 47, Supplement 2S93-S101 (1998).
Panglisch, Monafsschrift fuer Brauwissen Schaft, 1990, 43(1), 4-16.
Ringbom, et al. J. Nat Prod 61:1212-1215 (1998).
Pippa, et al. Scand. J. Gastroenterol. Suppl. 167:32-35 (1989).
Poullis, et al. J. Gastroenterol. Hepatol. 18:756-762 (2003).
Røseth, Digest. Liver Dis. 35:607-609 (2003).
Shah, et al. Gut 48:339-346 (2001).
Schjerven, et al. Br. J. Dermatol. 149:484-491 (2003).
Sivri, Fundam. Clinic. Pharmacol. 18:23-31 (2004).
Tagashira, et al. Biosci. Biotech. Biochem. 59(4):740-742 (1996).
Tibble, et al. Gut 45:362-366 (1999).
Tobe, et al. Biosci. Biotech. Biochem 61(1):158-159 (1997).
Yui, et al. Biol. Pharm. Bull. 26:753-760 (2003).
Warner, et al. Proc Natl Acad Sci USA 96:7563-7568 (1999).
Yamamoto, FEBS Letters 465:103-106 (2000).
"Information on Zyflamend and Zyflamend PM", downloaded from and Internet Aug. 30, 2002.
"Information on ArthroTrimTM product", downloaded from Internet Aug. 30, 2002.
Information on a book titled "Beyond Aspirin", by Thomas Newmark, et al., Release Jul. 2000; pp. 147-151, 248.
Germany, "The Absolutely German Drink," contents of beer, 2004, 5 pages.

* cited by examiner

COMPLEX MIXTURES EXHIBITING SELECTIVE INHIBITION OF CYCLOOXYGENASE-2

FIELD OF THE INVENTION

The present invention relates generally to a composition comprising a complex mixture of active ingredients exhibiting selective inhibition of inducible cyclooxygenase-2 (COX-2) and method for selective inhibition of COX-2 mediated synthesis of prostaglandins. More particularly, the composition comprises mixtures of active ingredients isolated from an extract of hops (Humulus lupulus). The composition functions to inhibit the inducibility and/or activity of inducible cyclooxygenase (COX-2) with little or no significant effect on constitutive cyclooxygenase (COX-1).

BACKGROUND OF THE INVENTION

Inflammatory diseases affect more than fifty million Americans. As a result of basic research in molecular and cellular immunology over the last ten to fifteen years, approaches to diagnosing, treating and preventing these immunologically-based diseases has been dramatically altered. One example of this is the discovery of an inducible form of the cyclooxygenase enzyme. Constitutive cyclooxygenase (COX), first purified in 1976 and cloned in 1988, functions in the synthesis of prostaglandins (PGs) from arachidonic acid(AA). Three years after its purification, an inducible enzyme with COX activity was identified and given the name COX-2, while constitutive COX was termed COX-1.

COX-2 gene expression is under the control of pro-inflammatory cytokines and growth factors. Thus, the inference is that COX-2 functions in both inflammation and control of cell growth. While COX-2 is inducible in many tissues, it is present constitutively in the brain and spinal cord, where it may function in nerve transmission for pain and fever. The two isoforms of COX are nearly identical in structure but have important differences in substrate and inhibitor selectivity and in their intracellular locations. Protective PGs, which preserve the integrity of the stomach lining and maintain normal renal function in a compromised kidney, are synthesized by COX-1. On the other hand, PGs synthesized by COX-2 in immune cells are central to the inflammatory process.

The discovery of COX-2 has made possible the design of drugs that reduce inflammation without removing the protective PGs in the stomach and kidney made by COX-1. Combinations of the invention would be useful for, but not limited to, the treatment of inflammation in a subject, and for treatment of other inflammation-associated disorders, such as, as an analgesic in the treatment of pain and headaches, or as an antipyretic for the treatment of fever. For example, combinations of the invention would be useful to treat arthritis, including but not limited to rheumatoid arthritis, spondyloarthopathies, gouty arthritis, osteoarthritis, systemic lupus erythematosus, and juvenile arthritis. Such combination of the invention would be useful in the treatment of asthma, bronchitis, menstrual cramps, tendonitis, bursitis, and skin related conditions such as psoriasis, eczema, burns and dermatitis. Combinations of the invention also would be useful to treat gastrointestinal conditions such as inflammatory bowel disease, Crohn's disease, gastritis, irritable bowel syndrome and ulcerative colitis and for the prevention or treatment of cancer such as colorectal cancer. Compositions of the invention would be useful in treating inflammation in such diseases as vascular diseases, migraine headaches, periarteritis nodosa, thyroiditis, aplastic anemia, Hodgkin's disease, sclerodma, rheumatic fever, type I diabetes, myasthenia gravis, multiple sclerosis, sacoidosis, nephrotic syndrome, Behchet's syndrome, polymyositis, gingivitis, hypersensitivity, swelling occurring after injury, myocardial ischemia and the like.

The compositions of the present invention would also be useful in the treatment of ophthalmic diseases, such as retinopathies, conjunctivitis, uveitis, ocular photophobia, and of acute injury to the eye tissue. The compounds would also be useful in the treatment of pulmonary inflammation, such as that associated with viral infections and cystic fibrosis. The compounds would also be useful for the treatment of certain nervous system disorders such as cortical dementias including Alzheimer's disease. The combinations of the invention are useful as anti-inflammatory agents, such as for the treatment of arthritis, with the additional benefit of having significantly less harmful side effects. As inhibitors of COX-2 mediated biosynthesis of PGE2, these compositions would also be useful in the treatment of allergic rhinitis, respiratory distress syndrome, endotoxin shock syndrome, atherosclerosis, and central nervous system damage resulting from stroke, ischemia and trauma.

Besides being useful for human treatment, these compounds are also useful for treatment of other animals, including horses, dogs, cats, birds, sheep, pigs, etc. An ideal formulation for the treatment of inflammation would inhibit the induction and activity of COX-2 without affecting the activity of COX-1. Historically, the non-steroidal and steroidal anti-inflammatory drugs used for treatment of inflammation lack the specificity of inhibiting COX-2 without affecting COX-1. Therefore, most anti-inflammatory drugs damage the gastrointestinal system when used for extended periods. Thus, new COX-2 specific treatments for inflammation and inflammation-based diseases are urgently needed.

Hop extraction in one form or another goes back over 150 years to the early nineteenth century when extraction in water and ethanol was first attempted. Even today an ethanol extract is available in Europe, but by far the predominant extracts are organic solvent extracts (hexane) and $CO_2$ extracts (supercritical and liquid). $CO_2$ (typically at 60 bars pressure and 5 to 10° C.) is in a liquid state and is a relatively mild, non-polar solvent highly specific for hop soft resins and oils. Beyond the critical point, typically at 300 bars pressure and 60° C., $CO_2$ has the properties of both a gas and a liquid and is a much stronger solvent. The composition of the various extracts is compared in Table 1.

TABLE 1

| | Hop Extracts (Percent W/W) | | | |
|---|---|---|---|---|
| Component | Hops | Organic Solvent Extract | Super-Critical $CO_2$ | Liquid $CO_2$ |
| Total resins | 12–20 | 15–60 | 75–90 | 70–95 |
| Alpha-acids | 2–12 | 8–45 | 27–55 | 30–60 |
| Beta-acids | 2–10 | 8–20 | 23–33 | 15–45 |
| Essential oils | 0.5–1.5 | 0–5 | 1–5 | 2–10 |
| Hard resins | 2–4 | 2–10 | 5–11 | None |
| Tannins | 4–10 | 0.5–5 | 0.1–5 | None |
| Waxes | 1–5 | 1–20 | 4–13 | 0–10 |
| Water | 8–12 | 1–15 | 1–7 | 1–5 |

At its simplest, hop extraction involves milling, pelleting and re-milling the hops to spread the lupulin, passing a solvent through a packed column to collect the resin components and finally, removal of the solvent to yield a whole or "pure" resin extract.

The main organic extractants are strong solvents and in addition to virtually all the lupulin components, they extract plant pigments, cuticular waxes, water and water-soluble materials.

Supercritical $CO_2$ is more selective than the organic solvents and extracts less of the tannins and waxes and less water and hence water-soluble components. It does extract some of the plant pigments like chlorophyll but rather less than the organic solvents do. Liquid $CO_2$ is the most selective solvent used commercially for hops and hence produces the most pure whole resin and oil extract. It extracts none of the hard resins or tannins, much lower levels of plant waxes, no plant pigments and less water and water-soluble materials.

As a consequence of this selectivity and the milder solvent properties, the absolute yield of liquid $CO_2$ extract per unit weight of hops is less than when using the other mentioned solvents. Additionally, the yield of alpha acids with liquid $CO_2$ (89–93%) is lower than that of supercritical $CO_2$ (91–94%) or the organic solvents (93–96%). Following extraction there is the process of solvent removal, which for organic solvents involves heating to cause volatilization. Despite this, trace amounts of solvent do remain in the extract. The removal of $CO_2$, however, simply involves a release of pressure to volatilize the $CO_2$.

The identification of humulone from hops extract as an inhibitor of bone resorption is reported in Tobe, H. et al. 1997. Bone resorption Inhibitors from hop extract. Biosci. Biotech. Biochem 61(1)158–159. Later studies by the same group characterized the mechanism of action of humulone as inhibition of COX-2 gene transcription following TNFalpha stimulation of MC3T3-E1 cells [Yamamoto, K. 2000. Suppression of cyclooxygenase-2 gene transcription by humulon of bee hop extract studied with reference to glucocorticoid. FEBS Letters 465:103–106].

Thus, it would be useful to identify a natural formulation of compounds that would specifically inhibit or prevent the synthesis of prostaglandins by COX-2 with little or no effect on COX-1. Such a formulation, which would be useful for preserving the health of joint tissues, for treating arthritis or other inflammatory conditions, has not previously been discovered. The term "specific or selective COX-2 inhibitor" embrace compounds or mixtures of compounds that selectively inhibit COX-2 over COX-1. Preferably, the compounds have a median effective concentration for COX-2 inhibition that is minimally five times greater than the median effective concentration for the inhibition of COX-1. For example, if the median inhibitory concentration for COX-2 of a test formulation was 0.2 μg/mL, the formulation would not be considered COX-2 specific unless the median inhibitory concentration for COX-1 was equal to or greater than 1 μg/mL.

While glucosamine is generally accepted as being effective and safe for treating osteoarthritis, medical intervention into the treatment of degenerative joint diseases is generally restricted to the alleviation of its acute symptoms. Medical doctors generally utilize non-steroidal and steroidal anti-inflammatory drugs for treatment of osteoarthritis. These drugs, however, are not well adapted for long-term therapy because they not only lack the ability to promote and protect cartilage; they can actually lead to degeneration of cartilage or reduction of its synthesis. Moreover, most non-steroidal, anti-inflammatory drugs damage the gastrointestinal system when used for extended periods. Thus, new treatments for arthritis are urgently needed.

The joint-protective properties of glucosamine would make it an attractive therapeutic agent for osteoarthritis except for two drawbacks: (1) the rate of response to glucosamine treatment is slower than for treatment with anti-inflammatory drugs, and (2) glucosamine may fail to fulfill the expectation of degenerative remission. In studies comparing glucosamine with non-steroidal anti-inflammatory agents, for example, a double-blinded study comparing 1500 mg glucosamine sulfate per day with 1200 mg ibuprofen, demonstrated that pain scores decreased faster during the first two weeks in the ibuprofen patients than in the glucosamine-treated patients. However, the reduction in pain scores continued throughout the trial period in patients receiving glucosamine and the difference between the two groups turned significantly in favor of glucosamine by week eight. Lopes Vaz, A., Double-blind clinical evaluation of the relative efficacy of ibuprofen and glucosamine sulphate in the management of osteoarthritis of the knee in outpatients, 8 Curr. Med Res Opin. 145–149 (1982). Thus, glucosamine may relieve the pain and inflammation of arthritis at a slower rate than the available anti-inflammatory drugs.

An ideal formulation for the normalization of cartilage metabolism or treatment of osteoarthritis would provide adequate chondroprotection with potent anti-inflammatory activity. The optimal dietary supplement for osteoarthritis should enhance the general joint rebuilding qualities offered by glucosamine and attenuate the inflammatory response without introducing any harmful side effects. It should be inexpensively manufactured and comply with all governmental regulations.

However, the currently available glucosamine formulations have not been formulated to optimally attack and alleviate the underlying causes of osteoarthritis and rheumatoid arthritis. Moreover, as with many commercial herbal and dietary supplements, the available formulations do not have a history of usage, nor controlled clinical testing, which might ensure their safety and efficacy.

Therefore, it would be useful to identify a composition that would specifically inhibit or prevent the expression of COX-2 enzymatic activity, while having little or no effect on COX-1 metabolism so that these could be used at sufficiently low doses or at current clinical doses with no adverse side effects.

SUMMARY OF THE INVENTION

The present invention provides a composition comprising an effective amount of component I selected from the group consisting of alpha acids and beta acids and an effective amount of at least one component II selected from the group consisting of alpha acids, beta acids, essential oils, fats and waxes, with the proviso that component I and II are not the same compound. Preferably, the composition comprises two or more active ingredients selected from the group consisting of ?-acid, ?-acid and essential oil. The active ingredients of the present invention are preferably made from hops extract. The composition functions synergistically to inhibit the activity of inducible COX-2 with little or no effect on COX-1.

The present invention further provides a composition of matter that enhances the function of glucosamine or chondrotin sulfate to normalize joint movement or reduce the symptoms of osteoarthritis.

One specific embodiment of the present invention is a composition comprising a 30 to 60 weight percent of α-acid, 15 to 45 weight percent of β-acid and 3 to 6 weight percent of essential oil. The composition optionally comprises 2 to 8 weight percent of fats and waxes. Preferably, the α-acid, β-acid, essential oil, fats or waxes are from a hops extract, which is preferably prepared by $CO_2$ extraction.

The present invention further provides a method of dietary supplementation and a method of treating inflammation or inflammation-based diseases in an animal which comprises providing to the animal suffering symptoms of inflammation, including pain and swelling, the composition of the present invention containing two or more active ingredients selected from the group consisting of α-acid, β-acid and essential oil and continuing to administer such a dietary supplementation of the composition until said symptoms are eliminated or reduced.

DETAILED DESCRIPTION OF THE INVENTION

Before the present composition and methods of making and using thereof are disclosed and described, it is to be understood that this invention is not limited to the particular configurations, as process steps, and materials may vary somewhat. It is also intended to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

The present invention provides a composition having a selective inhibitory effect on the activity of COX-2, said composition comprising an effective amount of component I selected from the group consisting of alpha acids and beta acids and an effective amount of at least one component II selected from the group consisting of alpha acids, beta acids, essential oils, fats and waxes, with the proviso that component I and II are not the same compound. More particularly, the composition comprises two or more active ingredients selected from the groups consisting of α-acids, β-acids and essential oils. Preferably, the active ingredients of the present invention are made from Hops extract. Preferably, composition comprising an 30 to 60 weight percent of α-acids, 15 to 45 weight percent of β-acids and 3 to 6 weight percent of essential oils. The composition optionally comprises 2 to 8 weight percent of fats and waxes. Preferably, the α-acids, β-acids, essential oils, fats or waxes are from a hop extract, which is preferably prepared by $CO_2$ extraction. The composition provided by the present invention can be formulated as a dietary supplement or therapeutic composition. The composition functions to inhibit the inducibility and/or activity of COX-2 with little or no effect on COX-1.

As used herein, the term "dietary supplement" refers to compositions consumed to affect structural or functional changes in physiology. The term "therapeutic composition" refers to any compounds administered to treat or prevent a disease.

As used herein, the term "COX inhibitor" refers to a composition of natural compounds that is capable of inhibiting the activity or expression of COX-2 enzymes or is capable of inhibiting or reducing the severity, including pain and swelling, of a severe inflammatory response.

As used herein, the term "hop extract" refers to the solid material resulting from (1) exposing a hops plant product to a solvent, (2) separating the solvent from the hops plant product, and (3) eliminating the solvent.

As used herein, the term "solvent" refers to a liquid of aqueous or organic nature possessing the necessary characteristics to extract solid material from the hop plant product. Examples of solvents would include water, steam, superheated water, methanol, ethanol, hexane, chloroform, liquid $CO_2$, liquid $N_2$ or any combinations of such materials.

As used herein, the term "$CO_2$ extract" refers to the solid material resulting from exposing a hops plant product to a liquid or supercritical $CO_2$ preparation followed by the removing the $CO_2$.

As used herein, the term "α-acid fraction" refers to compounds isolated from hops plant products including, among others, humulone, cohumulone, isohumulone, isoprehumulone, hulupone, adhumulone, xanthohumol A and xanthohumol B.

As used herein, the term "β-acid fraction" refers to compounds collectively known as lupulones including among others lupulone, colupulone, adlupulone, tetrahydroisohumulone, and hexahydrocolupulone, As used herein, the term "essential oil fraction" refers to a complex mixture of components consisting chiefly of myrcene, humulene, beta-caryophyleen, undecane-2-on, and 2-methyl-but-3-en-ol.

As used herein, the term "fats" refers to triacylglyerol esters of fatty acids.

As used herein, the term "waxes" refers to triacylglycerol ethers or esters of extremely long chain (>25 carbons) fatty alcohols or acids.

Therefore, one preferred embodiment of the present invention is a composition comprising a combination of an effective amount of two or more active ingredients selected from the group consisting of α-acid, β-acid and essential oil. The composition of the present invention functions to specifically inhibit the inducibility and/or activity of COX-2 while showing little or no effect on COX-1. Therefore, the composition of the present invention essentially eliminates the inflammatory response, including pain and swelling, rapidly without introducing any harmful side effects.

The pharmaceutical grade extract must pass extensive safety and efficacy procedures. Pharmaceutical grade $CO_2$ hops extract refers to a preparation wherein the concentration of hops extract, as employed in the practice of the invention, has an ?-acid content of about 10 to 95 percent by weight. Preferably, the β-acid content is greater than 45 percent by weight. The range of β-acid content in a pharmaceutical grade hops extract is about 10 to 95 percent by weight. Preferably, the ?-acid content is greater than 45 percent by weight. The pharmaceutical grade extracts are particularly preferred. A daily dose (mg/kg-day) of the present dietary supplement would be formulated to deliver, about 0.001 to 100 mg $CO_2$ extract of hops extract per kg body weight of the animal.

The composition of the present invention for topical application would contain about 0.001 to 10 wt %, preferably 0.01 to 1 wt % of pharmaceutical grade $CO_2$ hops extract.

The preferred composition of the present invention would produce serum or target tissue concentrations of any of the α-acid or β-acid components in the range of about 0.005 to 10,000 ng/mL.

In addition to the combination of component I selected from the group consisting of alpha acids and beta acids and at least one component II selected from the group consisting of alpha acids, beta acids, essential oils, fats and waxes, with the proviso that component I and II are not the same compound, the present composition for dietary application may include various additives such as other natural components of intermediary metabolism, vitamins and minerals, as well as inert ingredients such as talc and magnesium stearate that are standard excipients in the manufacture of tablets and capsules.

As used herein, "pharmaceutically acceptable carrier" includes any and all solvents, dispersion media, coatings, isotonic and absorption delaying agents, sweeteners and the like. These pharmaceutically acceptable carriers may be prepared from a wide range of materials including, but not limited to, diluents, binders and adhesives, lubricants, disintegrants, coloring agents, bulking agents, flavoring agents, sweetening agents and miscellaneous materials such as buffers and absorbents that may be needed in order to prepare a particular therapeutic composition. The use of such media and agents for pharmaceutically active substances is well known in the art. Except insofar as any conventional media or agent is incompatible with the active ingredients, its use in the present composition is contemplated. In one embodiment, talc and magnesium stearate are included in the present formulation. Other ingredients known to affect the manufacture of this composition as a dietary bar or functional food can include flavorings, sugars, amino-sugars, proteins and/or modified starches, as well as fats and oils.

The dietary supplements, lotions or therapeutic compositions of the present invention can be formulated in any manner known by one of skill in the art. In one embodiment, the composition is formulated into a capsule or tablet using techniques available to one of skill in the art. In capsule or tablet form, the recommended daily dose for an adult human or animal would preferably be contained in one to six capsules or tablets. However, the present compositions may also be formulated in other convenient forms, such as an injectable solution or suspension, a spray solution or suspension, a lotion, gum, lozenge, food or snack item. Food, snack, gum or lozenge items can include any ingestible ingredient, including sweeteners, flavorings, oils, starches, proteins, fruits or fruit extracts, vegetables or vegetable extracts, grains, animal fats or proteins. Thus, the present compositions can be formulated into cereals, snack items such as chips, bars, chewable candies or slowly dissolving lozenges.

The present invention contemplates treatment of all types of inflammation-based diseases, both acute and chronic. The present formulation reduces the inflammatory response and thereby promotes healing of, or prevents further damage to, the affected tissue. A pharmaceutically acceptable carrier may also be used in the present compositions and formulations.

According to the present invention, the animal may be a member selected from the group consisting of humans, non-human primates, such as dogs, cats, birds, horses, ruminants or other animals. The invention is directed primarily to the treatment of human beings. Administration can be by any method available to the skilled artisan, for example, by oral, topical, transdermal, transmucosal, or parenteral routes.

The following examples are intended to illustrate but not in any way limit the invention.

EXAMPLE 1

Selective Inhibition of Cyclooxygenase-2 Mediated Prostaglandin E2 by a $CO_2$ Extract of Hops This example illustrates a superior COX-2 selectivity of the $CO_2$ hops extract of the present invention compared to the pure compound humulone described in the prior art. Therefore it is to be inferred that the effectiveness of the CO2 hops extract of the present invention would be superior to the pure compound humulone described in the prior art.

Inhibition of COX-2 Mediated Production of PGE2 by $CO_2$ Extract of Hops

Equipment—balancer, analytical, Ohaus Explorer (Ohaus Model #EO1140, Switzerland), biosafety cabinet (Forma Model #F1214, Marietta, Ohio), pipettor, 100 to 1000 μL (VWR Catalog #4000-208, Rochester, N.Y.), cell hand tally counter (VWR Catalog #23609-102, Rochester, N.Y.), $CO_2$ incubator (Forma Model #F3210, Marietta, Ohio), hemacytometer (Hausser Model #1492, Horsham, Pa.), microscope, inverted (Leica Model #DM IL, Wetzlar, Germany), multichannel pipettor, 12-Channel (VWR Catalog #53501-662, Rochester, N.Y.), Pipet Aid (VWR Catalog #53498-103, Rochester, N.Y.), Pipettor, 0.5 to 10 μL (VWR Catalog #4000-200, Rochester, N.Y.), pipettor, 100 to 1000 μL (VWR Catalog #4000-208, Rochester, N.Y.), pipettor, 2 to 20 μL (VWR Catalog #4000-202, Rochester, N.Y.), pipettor, 20 to 200 μL (VWR Catalog #4000-204, Rochester, N.Y.), PURELAB Plus Water Polishing System (U.S. Filter, Lowell, Mass.), refrigerator, 4° C. (Forma Model #F3775, Marietta, Ohio), vortex mixer (VWR Catalog #33994-306, Rochester, N.Y.), water bath (Shel Lab Model #1203, Cornelius, Oreg.).

Cells, Chemicals, Reagents and Buffers—Cell scrapers (Corning Catalog #3008, Corning, N.Y.), dimethylsulfoxide (DMSO) (VWR Catalog #5507, Rochester, N.Y.), Dulbecco's Modification of Eagle's Medium (DMEM) (Mediatech Catalog #10-013-CV, Herndon, Va.), fetal bovine serum, heat inactivated (FBS-HI) (Mediatech Catalog #35-011-CV, Herndon, Va.), lipopolysaccharide (LPS) (Sigma Catalog #L-2654, St. Louis, Mo.), microfuge tubes, 1.7 mL (VWR Catalog #20172-698, Rochester, N.Y.), penicillin/streptomycin (Mediatech Catalog #30-001-CI, Herndon, Va.), pipet tips for 0.5 to 10 μL pipettor (VWR Catolog #53509-138, Rochester, N.Y.), pipet tips for 100–1000 μL pipettor (VWR Catolog #53512-294, Rochester, N.Y.), pipet tips for 2–20 μL and 20–200 μL pipettors (VWR Catolog #53512-260, Rochester, N.Y.), pipets, 10 mL (Becton Dickinson Catalog #7551, Marietta, Ohio), pipets, 2 mL (Becton Dickinson Catalog #7507, Marietta, Ohio, pipets, 5 mL (Becton Dickinson Catalog #7543, Marietta, Ohio), RAW 264.7 Cells (American Type Culture Collection Catalog #TIB-71, Manassas, Va.), test compounds (liquid $CO_2$ hops extract from Hopunion, Yakima, Wash.), tissue culture plates, 96-well (Becton Dickinson Catalog #3075, Franklin Lanes, N.J.), Ultra-pure water (Resistance=18 megaOhm-cm deionized water).

General Procedure—RAW 264.7 cells, obtained from ATCC, were grown in DMEM medium and maintained in log phase. The DMEM growth medium was made as follows: 50 mL of heat inactivated FBS and 5 mL of penicillin/streptomycin was added to a 500 mL bottle of DMEM and stored at 4° C. For best result the medium is to be used within three months and warmed to 37° C. in water bath before use.

On day one of the experiment, the log phase 264.7 cells were plated at 8×10⁴ cells per well in 0.2 mL growth medium per well in a 96-well tissue culture plate in the morning. At the end of the day 1 (6 to 8 hours post plating), 100 µL of growth medium from each well were removed and replaced with 100 µL fresh medium. A 1.0 mg/mL solution of LPS, which is used to induce the expression of COX-2 in the RAW 264.7 cells, was prepared by dissolving 1.0 mg of LPS in 1 mL DMSO. It was vortexed until it dissolved and was stored at 4° C. Melt at room temperature or in a 37° C. water bath before use. Make up a new solution every 60 days.

On day two of the experiment, liquid $CO_2$ hops extract was prepared as 1000× stock in DMSO. For example, if the final concentration of the test material is to be 10 µg/mL, a 10 mg/mL stock should be prepared by dissolving 10 mg of the test material in 1 mL of DMSO. For the best result, fresh liquid $CO_2$ hops extract should be prepared on the day of the experiment. In 1.7 mL microfuge tubes, 1 mL DMEM without FBS was added for test concentrations of 0.05, 0.10, 0.5, and 1.0 µg/mL. 2 µL of the 1000×DMSO stock of the test material was added to the 1 mL of medium without FBS. The tube contained the final concentration of the test material concentrated 2-fold and placed tube in an incubator for 10 minutes to equilibrate.

One-hundred microliters of medium was removed from each well of the cell plates prepared on day one. One-hundred microliter of equilibrated 2× final concentration the test compounds was added to cells and incubated for 90 minutes. LPS in DMEM without FBS was prepared by adding 44 µL of the 1 mg/mL DMSO stock to 10 mL of medium. For each well of cells to be stimulated, 20 µL of LPS (final concentration of LPS is 0.4 µg/mL of LPS) was added and incubated for 24 hours.

On day 3, the appearance of the cells was observed. One-hundred microliter supernatent medium from each well was transferred to a clean microfuge tube for the determination of amount of PGE2 in the medium.

Determination of COX-1 Enzyme Inhibition by Hops Extract

The ability of a test material to inhibit COX-1 synthesis of PGE2 was determined essentially as described by Noreen, Y., et al. (J. Nat. Prod. 61, 2–7, 1998).

Equipment—balancer (2400 g, Acculab VI-2400, VWR Catalog #11237-300, Rochester, N.Y.), balancer, analytical, Ohaus Explorer (Ohaus Model #EO1140, Switzerland), biosafety cabinet (Forma Model #F1214, Marietta, Ohio), Freezer, −30° C. (Forma Model #F3797), Freezer, −80° C. Ultralow (Forma Model #F8516, Marietta, Ohio), heated stirring plate (VWR Catalog #33918-262, Rochester, N.Y.), ice maker (Scotsman Model #AFE400A-1A, Fairfax, S.C.), multichannel pipettor, 12-Channel (VWR Catalog #53501-662, Rochester, N.Y.), Multichannel Pipettor, 8-Channel (VWR Catalog #53501-660, Rochester, N.Y.), orbital shaker platform (Scienceware #F37041-0000, Pequannock, N.J.), pH meter (VWR Catalog #33221-010, Rochester, N.Y.), pipet aid (VWR Catalog #53498-103, Rochester, N.Y.), pipettor, 0.5 to 10 µL (VWR Catalog #4000-200, Rochester, N.Y.), pipettor, 100 to 1000 µL (VWR Catalog #4000-208, Rochester, N.Y.), pipettor, 2 to 20 µL (VWR Catalog #4000-202, Rochester, N.Y.), pipettor, 20 to 200 µL (VWR Catalog #4000-204, Rochester, N.Y.), PURELAB Plus Water Polishing System (U.S. Filter, Lowell, Mass.), refrigerator, 4° C. (Forma Model #F3775, Marietta, Ohio), vacuum chamber (Sigma Catalog #Z35, 4074, St. Louis, Mo.), vortex mixer (VWR Catalog #33994-306, Rochester, N.Y.)

Supplies and Reagents—96-Well, round-bottom plate (Nalge Nunc #267245, Rochester, N.Y.), arachidonic acid (Sigma Catalog #A-3925, St. Louis, Mo.), centrifuge tubes, 15 mL, conical, sterile (VWR Catalog #20171-008, Rochester, N.Y.), COX-1 enzyme (ovine) 40,000 units/mg (Cayman Chemical Catalog #60100, Ann Arbor, Mich.), dimethylsulfoxide (DMSO) (VWR Catalog #5507, Rochester, N.Y.), ethanol 100% (VWR Catalog #MK701908, Rochester, N.Y.), epinephrine (Sigma Catalog #E-4250, St. Louis, Mo.), glutathione (reduced) (Sigma Catalog # G-6529, St. Louis, Mo.), graduated cylinder, 1000 mL (VWR Catalog #24711-364, Rochester, N.Y.), hematin (porcine) (Sigma catalog # H-3281, St. Louis, Mo.), hydrochloric acid (HCl) (VWR Catalog #VW3110-3, Rochester, N.Y.), Kim Wipes (Kimberly Clark Catalog #34256, Roswell, Ga.), microfuge tubes, 1.7 mL (VWR Catalog #20172-698, Rochester, N.Y.), NaOH (Sigma Catalog #S-5881, St. Louis, Mo.), pipet tips for 0.5 to 10 µL pipettor (VWR Cotolog #53509-138, Rochester, N.Y.), pipet tips for 100–1000 µL pipettor (VWR Catolog #53512-294, Rochester, N.Y.), pipet tips for 2–20 µL and 20–200 µL pipettors (VWR Cotolog #53512-260, Rochester, N.Y.), prostaglandin E2 (Sigma Catalog # P-5640, St. Louis, Mo.), prostaglandin F2alpha (Sigma Catalog # P-0424, St. Louis, Mo.), stir bar, magnetic (VWR Catalog #58948-193, Rochester, N.Y.), storage bottle, 1000 mL (Corning Catalog #1395-1L, Corning, N.Y.), storage bottle, 100 mL (Corning Catalog #1395-100, Corning, N.Y.), $CO_2$ extract of hops (Hopunion, Yakima, Wash.), Tris-HCl (Sigma Catalog #T-5941, St. Louis, Mo.), ultrapure water (Resistance=18 megaOhm-cm deionized water).

General Procedure—Oxygen-free 1.0M Tris-HCl buffer (pH 8.0) was prepared as follows: In a 1000 mL beaker, 12.11 g Trizma HCl was dissolved into 900 mL ultra-pure water. The beaker was placed on a stir plate with a stir bar. NaOH was added until the pH reached 8.0. The volume was adjusted to a final volume of 1000 mL and stored in a 1000 mL storage bottle.

The Tris-HCl buffer was placed into a vacuum chamber with a loose top and the air pump was turned on until the buffer stopped bubbling. The vacuum chamber was turned off and the storage bottle was covered tight. This step was repeated each time when the oxygen-free Tris-HCl buffer was used.

1 mL cofactor solution was prepared by adding 1.3 mg (−) epinephrine, 0.3 mg reduced glutathione and 1.3 mg hematin to 1 mL oxygen free Tris-HCl buffer. Solutions of the test material were prepared as needed. i.e. 10 mg of aspirin was weighed and dissolved into 1 mL DMSO.

Enzyme was dissolved in oxygen free Tris-HCl buffer as follows, i.e. on ice, 6.5 µL of enzyme at 40,000 units/mL was taken and added to 643.5 µL of oxygen free Tris-HCl buffer. This enzyme solution is enough for 60 reactions. The COX-1 enzyme solution was prepared as follows. in a 15 mL centrifuge tube, 10 µL COX-1 enzyme at 40,000 units/mL was added in oxygen free Tris-HCl with 50 µL of the cofactor solution per reaction. The mixture was incubated on ice for 5 minutes (i.e. for 60 reactions add 650 µl enzyme in oxygen free Tris-HCl buffer with 3.25 mL cofactor solution).

60 µl of the enzyme solution was combined with 20 µl of the test solution in each well of a 96 well plate. Final concentrations of the test solutions were 100, 50, 25, 12.5, 6.25 and 3.12 µg/mL. The plates were preincubated on ice for 10 minutes. 20 µL arachidonic acid (30 µM) was added and incubated for 15 minutes at 37° C.

2 M HCl was prepared by diluting 12.1 N HCl. In a 100 mL storage bottle, 83.5 mL ultra-pure water was added and then 16.5 mL 12.1 N HCl was added. It was stored in a 100 mL storage bottle and placed in the biosafty cabinet (always add acid last). The reaction was terminated by adding 10 μL 2 M HCl. The final solution was used as the supernate for the $PGE_2$ assay.

Determination of PGE2 Concentration in Medium

The procedure followed was that essentially described by Hamberg, M. and Samuelsson, B. (J. Biol. Chem. 1971. 246, 6713–6721); however a commercial, nonradioactive procedure was employed.

Equipment—freezer, −30° C. (Forma Model #F3797), heated stirring plate (VWR Catalog #33918-262, Rochester, N.Y.), multichannel pipettor, 12-Channel (VWR Catalog #53501-662, Rochester, N.Y.), orbital shaker platform (Scienceware #F37041-0000, Pequannock, N.J.), Pipet Aid (VWR Catalog #53498-103, Rochester, N.Y.), pipettor, 0.5 to 10 μL (VWR Catalog #4000-200, Rochester, N.Y.), pipettor, 100 to 1000 μL (VWR Catalog #4000-208, Rochester, N.Y.), pipettor, 2 to 20 μL (VWR Catalog #4000-202, Rochester, N.Y.), pipettor, 20 to 200 μL (VWR Catalog #4000-204, Rochester, N.Y.), plate reader (Bio-tek Instruments Model #E1x800, Winooski, Vt.), PURELAB Plus Water Polishing System (U.S. Filter, Lowell, Mass.), refrigerator, 4° C. (Forma Model #F3775, Marietta, Ohio).

Chemicals, Reagents and Buffers—Prostaglandin $E_2$ EIA Kit-Monoclonal 480-well (Cayman Chemical Catalog #514010, Ann Arbor, Mich.), centrifuge tube, 50 mL, conical, sterile (VWR Catalog #20171-178, Rochester, N.Y.), Dulbecco's Modification of Eagle's Medium (DMEM) (Mediatech Catalog #10-013-CV, Herndon, Va.), graduated cylinder, 100 mL (VWR Catalog #24711-310, Rochester, N.Y.), Kim Wipes (Kimberly Clark Catalog #34256, Roswell, Ga.), microfuge tubes, 1.7 mL (VWR Catalog #20172-698, Rochester, N.Y.), penicillin/streptomycin (Mediatech Catalog #30-001-CI, Herndon, Va.), pipet tips for 0.5 to 10 μL pipettor (VWR Catolog #53509-138, Rochester, N.Y.), pipet tips for 100–1000 μL pipettor (VWR Catolog #53512-294, Rochester, N.Y.), pipet tips for 2–20 μL and 20–200 μL pipettors (VWR Catolog #53512-260, Rochester, N.Y.), pipets, 25 mL (Becton Dickinson Catalog #7551, Marietta, Ohio), storage bottle, 100 mL (Corning Catalog #1395-100, Corning, N.Y.), storage bottle, 1000 mL (Corning Catalog #1395-1L, Corning, N.Y.), ultra-pure water (Resistance=18 megaOhm-cm deionized water).

General Procedure—EIA Buffer was prepared by diluting the contents of EIA Buffer Concentrate (vial #4) with 90 ml of Ultra-pure water. The vial #4 was rinsed several times to ensure all crystals had been removed and was placed into a 100 mL storage bottle and stored at 4° C.

The Wash Buffer was prepared by diluting Wash Buffer Concentrate (vial #5) 1:400 with Ultra-pure water. 0.5 ml/liter of Tween 20 (vial #5a) was then added (using a syringe for accurate measurement). i.e. (For one liter Wash Buffer add 2.5 ml Wash Buffer Concentrate, 0.5 ml Tween-20, and 997 ml Ultra-pure water.) The solution was stored in a 1 liter storage bottle at 4° C.

The Prostaglandin $E_2$ standard was reconstituted as follows. A 200 μL pipet tip was equilibrated by repeatedly filling and expelling the tip several times in ethanol. The tip was used to transfer 100 μL of the $PGE_2$ Standard (vial #3) into a 1.7 mL microfuge tube. 900 μl Ultra-pure water was added to the tube and stored at 4° C., which was stable for ~6 weeks.

The Prostaglandin $E_2$ acetylcholinesterase tracer was reconstituted as follows. 100 μL $PGE_2$ tracer (vial #2) was taken and mixed with 30 mL of the EIA Buffer in a 50 mL centrifuge tube and stored at 4° C. The solution should be used within five weeks.

The Prostaglandin $E_2$ monoclonal antibody was reconstituted as follows. 100 μL $PGE_2$ Antibody (vial #1) was taken and mixed with 30 mL of the EIA buffer in a 50 mL centrifuge tube and stored at 4° C. This solution should be used up within 5 weeks.

DMEM with penicillin/streptomycin was prepared by adding 5 mL penicillin/streptomycin into 500 mL DMEM and stored at 4° C.

The plate was set up as follows: Each plate contained a minimum of two blanks (B), two non-specific binding wells (NSB), two maximum binding wells ($B_0$), and an eight point standard curve run in duplicate (S1–S8). Each sample was assayed at a minimum of two dilutions and each dilution was run in duplicate.

The standard was prepared as follows: Eight 1.7 mL microuge tubes were labeled as tube 1–8. 900 μL DMEM into was put in tube 1 and 500 μL DMEM into tubes 2–8. 100 μL of the $PGE_2$ standard was put into tube 1 and mixed. Five-hundred microliter solution was taken from tube 1 and put into tube 2 and this process was repeated through tube 8.

Fifty microliters of EIA Buffer and 50 μl DMEM were added into the NSB wells. Fifty μl DMEM was added to the $B_0$ wells. Fifty microliters of solution was taken from tube #8 and added to both the lowest standard wells (S8). Fifty microliters was taken from tube #7 and added to each of the next two wells. Continue this through to tube #1. (Use the same pipet tip for all 8 of the standards. Make sure to equilibrate the tip in each new standard by pipeting up and down in that standard. Using a P200, add 50 μl of each sample at each dilution to the sample wells).

Using the 12 channel pipetor, 50 μl of the Prostaglandin $E_2$ acetylcholinesterase tracer was added to each well except the Total Activity (TA) and the Blank (B) wells. Using the 12 channel pipetor, 50 μl of the Prostaglandin $E_2$ monoclonal antibody was added to each well except the Total Activity (TA), the (NSB), and the Blank (B) wells. The plate was covered with plastic film (item #7) and incubated for 18 hours at 4° C.

The plate was developed as follows: one 100 μL vial of Ellman's Reagent (vial #8) was reconstituted with 50 ml of Ultra-pure water in a 50 mL centrifuge tube. It was protected from light and used the same day. The wells were and rinsed five times with Wash Buffer using a 12 channel pipettor. Two-hundred microliters of Ellman's Reagent was added to each well using a 12 channel pipettor and 5 μl of Tracer to the (TA) well was then added to each well using a P10. The plate was covered with a plastic film and placed on orbital shaker in the dark for 60–90 minutes.

The plate was read in the Bio-tek plate reader at a single wavelength between 405 and 420 nm. Before reading each plate, the bottom was wiped with a Kim wipe. The plate should be read when the absorbance of the wells is in the range of 0.3–0.8 A.U. If the absorbance of the wells exceeds 1.5, wash and add fresh Ellmans' Reagent and redevelop.

The medium inhibitory concentration of the $CO_2$ hops extract for both COX-2 and COX-1 were assessed using CalcuSyn (BIOSOFT, biosoft.com). This statistical package performs multiple drug dose-effect calculations using the Median Effect methods described by T-C Chou and P. Talaly (Trends Pharmacol. Sci. 4:450–454). Briefly, it correlates the "Dose" and the "Effect" in the simplest possible form: $fa/fu=(C/Cm)^m$, where C is the concentration or dose of the compound and Cm is the median-effective dose signifying the potency. Cm is determined from the x-intercept of the median-effect plot. The fraction affected by the concentration of the test material is fa and the fraction unaffected by the concentration is fu (fu=1−fa). The exponent m is the parameter signifying the sigmoidicity or shape of the dose-effect curve. It is estimated by the slope of the median-effect plot.

The median-effect plot is a plot of x=log(C) vs y=log(fa/fu) and is based on the logarithmic form of Chou's median-effect equation. The goodness of fit for the data to the median-effect equation is represented by the linear correlation coefficient r of the median-effect plot. Usually, the experimental data from enzyme or receptor systems have r>0.96, from tissue culture or enzyme work.

The medium inhibitory concentration of COX-2 inhibition by the CO2-extract of hops in the RAW 264.7 cell model was 0.0.24 µg/mL (95% CI=0.16–0.36). The same CO2 extract of hops demonstrated a median inhibitory concentration of COX-1 production of PGE2 of 25.5 µg/mL. Thus, a COX-1/COX-2 specificity of 106 is observed. This COX-2 specificity is 2.7-fold greater than the COX-2 specificity demonstrated for pure humulone in the TNFalpha stimulation of MC3T3-E1 cells [Yamamoto, K 2000. Suppression of cyclooxygenase-2 gene transcription by humulon of bee hop extract studied with reference to glucocorticoid. FEBS Letters 465:103–106]. Such a large difference in COX-2 specificity between the pure compound and the complex mixture is unexpected and constitutes a novel finding. It is unusual that a complex mixture would contain greater specific biological activity than the most active molecule. The inference is that an underlying synergy among the bioactive molecules, including humulone, is to account for such an effect.

We claim:

1. A method of treating inflammation comprising administering to an animal suffering symptoms of inflammation a pharmaceutical grade extract of hops comprising an effective amount of tetrahydroisohumulone, and an effective amount of essential oils, fats or waxes, wherein said administration provides about 0.01 to 100 mg per kg body weight per day of tetrahydroisohumulone.

2. The method of claim 1, wherein the animal displays symptoms of acne rosacea.

3. The method of claim 1, wherein the animal displays symptoms of psoriasis.

4. The method of claim 1, wherein the animal displays symptoms of eczema.

5. The method of claims 1–4, wherein said administration provides 0.01 to 100 mg per kg body weight per day of essential oils.

6. The method of any one of claims 1–4, wherein said animal is selected from the group consisting of humans, non-human primates, dogs, cats, birds, horses, reptiles, fish, amphibians and ruminants.

7. The method of any one of claims 1–4, wherein administration is by a means selected from the group consisting of oral, parenteral, topical, transdermal and transmucosal delivery.

8. The method of any one of claims 1–4, wherein said administration is topical.

9. The method of any one of claims 1–4, wherein said pharmaceutical acceptable carrier is selected from the group consisting of coatings, isotonic and absorption delaying agents, binders and adhesives, lubricants, disintegrants, coloring agents, flavoring agents, sweetening agents, absorbants, detergents, and emulsifying agents.

10. The method of any one of claims 1–4, wherein said pharmaceutical grade extract of hops further comprises one or more members selected from the group consisting of antioxidants, vitamins and minerals.

11. The method of any one of claims 1–4, wherein said pharmaceutical grade extract of hops further comprises one or more members selected from the group consisting of proteins, fats, carbohydrates, glucosamine, chondrotin sulfate and amino sugars.

* * * * *